United States Patent

Müller et al.

[11] Patent Number: 6,136,840
[45] Date of Patent: Oct. 24, 2000

[54] FUNGICIDAL MIXTURES

[75] Inventors: Bernd Müller, Frankenthal; Hubert Sauter, Mannheim; Eberhard Ammermann, Heppenheim; Gisela Lorenz, Neustadt; Siegfried Strathmann, Limburgerhof; Maria Scherer, Landau; Klaus Schelberger, Gönnheim; Joachim Leyendecker, Ladenburg, all of Germany

[73] Assignee: BASF Aktiengesellschaft, Ludwigshafen, Germany

[21] Appl. No.: 09/242,671

[22] PCT Filed: Aug. 21, 1997

[86] PCT No.: PCT/EP97/04540

§ 371 Date: Feb. 22, 1999

§ 102(e) Date: Feb. 22, 1999

[87] PCT Pub. No.: WO98/08384

PCT Pub. Date: Mar. 5, 1998

[51] Int. Cl.[7] .......................... A01N 37/34; A01N 43/56; A01N 43/64
[52] U.S. Cl. ........................... 514/407; 514/383; 514/525
[58] Field of Search ..................................... 514/383, 407, 514/525

[56] References Cited

FOREIGN PATENT DOCUMENTS

| 741970 | 11/1996 | European Pat. Off. . |
|---|---|---|
| 2433907 | 3/1980 | France . |
| 4423613 | 1/1996 | Germany . |
| 96/01256 | 1/1996 | WIPO . |
| 96/01258 | 1/1996 | WIPO . |

OTHER PUBLICATIONS

Tomlin, The Pesticide Manual Incorporating The Agrochemicals Handbook 10th Ed (1995) pp. 193–195.

Primary Examiner—Allen J. Robinson
Attorney, Agent, or Firm—Keil & Weinkauf

[57] ABSTRACT

The present invention relates to a fungicidal mixture which comprises a) a carbamate of the formula I:

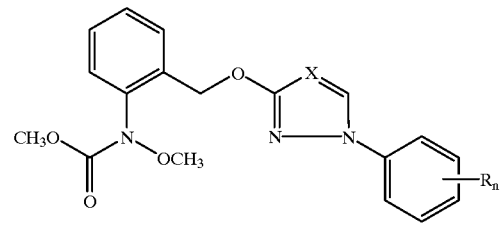

(I)

where X is CH and N, n is 0, 1 or 2 and R is halogen, $C_1$–$C_4$-alkyl and $C_1$–$C_4$-haloalkyl, it being possible for the radicals R to be different if n is 2, or a salt or adduct thereof, and b) tetrachloroisophthalonitrile II:

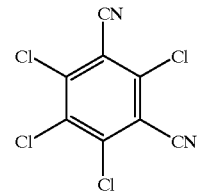

(II)

in a synergistically active amount.

8 Claims, No Drawings

FUNGICIDAL MIXTURES

This application is a 371 of PCT/EP 97/04540, filed Aug. 21, 1997.

The present invention relates to a fungicidal mixture which comprises a) a carbamate of the formula I:

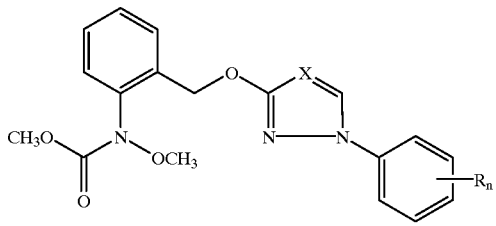

where X is CH and N, n is 0, 1 or 2 and R is halogen, $C_1$–$C_4$-alkyl and $C_1$–$C_4$-haloalkyl, it being possible for the radicals R to be different if n is 2, or a salt or adduct thereof, and b) tetrachlorisophthalonitrile II:

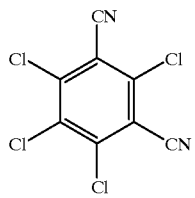

in a synergistically active amount.

Moreover, the invention relates to methods of controlling harmful fungi with mixtures of the compounds I and II and to the use of the compound I and the compound II for the preparation of such mixtures.

The compounds of the formula I, their preparation and their action against harmful fungi has been disclosed in the literature (PCT WO 96/01,256 and WO 96/01,258).

The compounds II (common name: chlorothalonil), their preparation and their action against harmful fungi is also disclosed (cf. "Pesticide Manual", page 193).

It is an object of the present invention to provide mixtures which have an improved activity against harmful fungi combined with a reduced total amount of active ingredients applied (synergistic mixtures) with a view to reducing the rates of application and to improving the spectrum of action of the known compounds I and II.

Accordingly, we have found that this object is achieved by the mixture defined at the outset. Moreover, we have found that better control of harmful fungi is possible by applying the compound I and the compound II simultaneously, ie. together or separately, or by applying the compound I and the compound II in succession than when the individual compounds are used on their own.

In particular, the formula I represents carbamates where the combination of the substituents corresponds to one line of the following table:

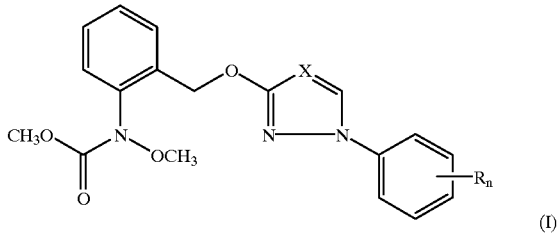

| No. | X | $R_n$ |
|---|---|---|
| I.1 | N | 2-F |
| I.2 | N | 3-F |
| I.3 | N | 4-F |
| I.4 | N | 2-Cl |
| I.5 | N | 3-Cl |
| I.6 | N | 4-Cl |
| I.7 | N | 2-Br |
| I.8 | N | 3-Br |
| I.9 | N | 4-Br |
| I.10 | N | 2-$CH_3$ |
| I.11 | N | 3-$CH_3$ |
| I.12 | N | 4-$CH_3$ |
| I.13 | N | 2-$CH_2CH_3$ |
| I.14 | N | 3-$CH_2CH_3$ |
| I.15 | N | 4-$CH_2CH_3$ |
| I.16 | N | 2-$CH(CH_3)_2$ |
| I.17 | N | 3-$CH(CH_3)_2$ |
| I.18 | N | 4-$CH(CH_3)_2$ |
| I.19 | N | 2-$CF_3$ |
| I.20 | N | 3-$CF_3$ |
| I.21 | N | 4-$CF_3$ |
| I.22 | N | 2,4-$F_2$ |
| I.23 | N | 2,4-$Cl_2$ |
| I.24 | N | 3,4-$Cl_2$ |
| I.25 | N | 2-Cl, 4-$CH_3$ |
| I.26 | N | 3-Cl, 4-$CH_3$ |
| I.27 | CH | 2-F |
| I.28 | CH | 3-F |
| I.29 | CH | 4-F |
| I.30 | CH | 2-Cl |
| I.31 | CH | 3-Cl |
| I.32 | CH | 4-Cl |
| I.33 | CH | 2-Br |
| I.34 | CH | 3-Br |
| I.35 | CH | 4-Br |
| I.36 | CH | 2-$CH_3$ |
| I.37 | CH | 3-$CH_3$ |
| I.38 | CH | 4-$CH_3$ |
| I.39 | CH | 2-$CH_2CH_3$ |
| I.40 | CH | 3-$CH_2CH_3$ |
| I.41 | CH | 4-$CH_2CH_3$ |
| I.42 | CH | 2-$CH(CH_3)_2$ |
| I.43 | CH | 3-$CH(CH_3)_2$ |
| I.44 | CH | 4-$CH(CH_3)_2$ |
| I.45 | CH | 2-$CF_3$ |
| I.46 | CH | 3-$CF_3$ |
| I.47 | CH | 4-$CF_3$ |
| I.48 | CH | 2,4-$F_2$ |
| I.49 | CH | 2,4-$Cl_2$ |
| I.50 | CH | 3,4-$Cl_2$ |
| I.51 | CH | 2-Cl, 4-$CH_3$ |
| I.52 | CH | 3-Cl, 4-$CH_3$ |

Especially preferred are the compounds I.12, I.23, I.32 and I.38.

Due to the basic character of the nitrogen compounds which they contain, the compounds I are capable of forming salts or adducts with inorganic or organic acids or with metal ions.

Examples of inorganic acids are hydrohalic acids, such as hydrofluoric acid, hydrochloric acid, hydrobromic acid and hydroiodic acid, sulfuric acid, phosphoric acid and nitric acid.

Suitable organic acids are, for example, formic acid, carbonic acid and alkanoic acids such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals of from 1 to 20 carbon atoms), arylsulfonic acids or -disulfonic acids (aromatic radicals such as phenyl and naphthyl which have attached to them one or two sulfo groups), alkylphosphonic acids (phosphonic acids having straight-chain or branched alkyl radicals of from 1 to 20 carbon atoms), arylphosphonic acids or -diphosphonic acids (aromatic radicals such as phenyl and naphthyl which have attached to them one or two phosphoric acid radicals), it being possible for the alkyl or aryl radicals to have attached to them further substituents, eg. p-toluenesulfonic acid, salicylic acid, p-aminosalicylic acid, 2-phenoxybenzoic acid, 2-acetoxybenzoic acid etc.

Suitable metal ions are, in particular, the ions of the elements of the first to eighth sub-group, mainly chromium, manganese, iron, cobalt, nickel, copper, zinc and also of the second main group, mainly calcium and magnesium, and of the third and fourth main group, in particular aluminum, tin and lead. The metals can in this case be in the various valences which they can assume.

When preparing the mixtures, it is preferred to employ the pure active ingredients I and II, with which further active ingredients against harmful fungi or against other pests such as insects, arachnids or nematodes, or else herbicidal or growth-regulating active ingredients or fertilizers can be admixed.

The mixtures of the compounds I and II, or the simultaneous, joint or separate use of the compounds I and II, are distinguished by an outstanding activity against a broad spectrum of phytopathogenic fungi, in particular from the classes of the Ascomycetes, Basidiomycetes, Phycomycetes and Deuteromycetes. Some of them act systemically and can therefore also be employed as foliar- and soil-acting fungicides.

They are especially important for controlling a large number of fungi in a variety of crop plants such as cotton, vegetable species (eg. cucumbers, beans, tomatoes, potatoes and cucurbits), barley, grass, oats, bananas, coffee, maize, fruit species, rice, rye, soybeans, grapevines, wheat, ornamentals, sugar cane, and a variety of seeds.

They are particularly suitable for controlling the following phytopathogenic fungi: *Erysiphe graminis* (powdery mildew) on cereals, *Erysiphe cichoracearum* and *Sphaerotheca fuliginea* on cucurbits, *Podosphaera leucotricha* on apples, *Uncinula necator* on grapevines, Puccinia species on cereals, Rhizoctonia species on cotton, rice and lawns, Ustilago species on cereals and sugar cane, *Venturia inaequalis* (scab) on apples, Helminthosporium species on cereals, *Septoria nodorum* on wheat, *Botrytis cinera* (gray mold) on strawberries, vegetables, ornamentals and grapevines, *Cercospora arachidicola* on peanuts, *Pseudocercosporella herpotrichoides* on wheat and barley, *Pyricularia oryzae* on rice, *Phytophthora infestans* on potatoes and tomatoes, *Plasmopara viticola* on grapevines, Pseudocercosporella species in hops and cucumbers, Alternaria species on vegetables and fruit, Mycosphaerella species in bananas and Fusarium and Verticillium species.

Furthermore, they can be used in the protection of materials (eg. in the protection of wood), for example against *Paecilomyces variotii*.

The compounds I and II can be applied simultaneously, ie. together or separately, or in succession, the sequence, in the case of separate application, generally not having any effect on the result of the control measures.

The compounds I and II are normally used in a weight ratio of from 10:1 to 0.025:1, preferably 5:1 to 0.05:1, in particular 1:1 to 0.05:1.

The application rates of the mixtures according to the invention are, especially for agricultural land, from 0.01 to 8 kg/ha, preferably 0.1 to 5 kg/ha, in particular 0.5 to 3.0 kg/ha, depending on the nature of the desired effect.

In the case of the compounds I, the application rates are from 0.01 to 2.5 kg/ha, preferably 0.05 to 2.5 kg/ha, in particular 0.1 to 1.0 kg/ha.

Correspondingly, in the case of the compounds II, the application rates are from 0.01 to 10 kg/ha, preferably 0.05 to 5 kg/ha, in particular 0.05 to 2.0 kg/ha.

For seed treatment, the application rates of the mixture are generally from 0.001 to 250 g/kg seed, preferably 0.01 to 100 g/kg, in particular 0.01 to 50 g/kg.

If the control measures are directed at phytopathogenic harmful fungi, the separate or joint application of the compounds I and II or of the mixtures of the compounds I and II is effected by spraying or dusting the seeds, the plants or the soils before or after sowing of the plants, or before or after plant emergence.

The fungicidal synergistic mixtures according to the invention, or the compounds I and II, can be formulated for example in the form of ready-to-spray solutions, powders and suspensions or in the form of highly concentrated aqueous, oily or other suspensions, dispersions, emulsions, oil dispersions, pastes, dusts, materials for spreading or granules, and applied by spraying, atomizing, dusting, spreading or pouring. The use form depends on the intended purpose; in any case, it should guarantee as fine and uniform as possible a distribution of the mixture according to the invention.

The formulations are prepared in a manner known per se, eg. by adding solvents and/or carriers. It is usual to admix inert additives, such as emulsifiers or dispersants, with the formulations.

Suitable surfactants are the alkali metal salts, alkaline earth metal salts and ammonium salts of aromatic sulfonic acids, eg. ligno-, phenol-, naphthalene- and dibutylnaphthalenesulfonic acid, and of fatty acids, of alkyl- and alkylarylsulfonates, of alkyl, lauryl ether and fatty alcohol sulfates, and salts of sulfated hexa-, hepta- and octadecanols or fatty alcohol glycol ethers, condensates of sulfonated naphthalene and its derivatives with formaldehyde, condensates of naphthalene, or of the naphthalenesulfonic acids, with phenol and formaldehyde, polyoxyethylene octylphenol ether, ethoxylated isooctyl-, octyl- or nonylphenol, alkylphenol polyglycol ethers or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene, lauryl alcohol polyglycol ether acetate, sorbitol esters, ligninsulfite waste liquors or methylcellulose.

Powders, materials for spreading and dusts can be prepared by mixing or jointly grinding the compounds I or II or the mixture of the compounds I and II with a solid carrier.

Granules (eg. coated granules, impregnated granules or homogeneous granules) are normally prepared by binding the active ingredient, or active ingredients, to a solid carrier.

Fillers or solid carriers are, for example, mineral earths such as silica gel, silicas, silica gels, silicates, talc, kaolin, limestone, lime, chalk, bole, loess, clay, dolomite, diatomaceous earth, calcium sulfate, magnesium sulfate, magnesium oxide, ground synthetic materials, and fertilizers such as ammonium sulfate, ammonium phosphate, ammonium nitrate, ureas, and products of vegetable origin such as cereal meal, tree bark meal, wood meal and nutshell meal, cellulose powders or other solid carriers.

The formulations generally comprise from 0.1 to 95% by weight, preferably 0.5 to 90% by weight, of one of the compounds I or II, or of the mixture of the compounds I and II. The active ingredients are employed in a purity of from 90% to 100%, preferably 95% to 100% (according to NMR or HPLC spectrum [sic]).

The compounds I or II, or the mixtures, or the corresponding formulations, are applied by treating the harmful fungi, their environment, or the plants, seeds, soils, areas, materials or spaces to be kept free from them with a fungicidally active amount of the mixture, or of the compounds I and II in the case of separate application.

Application can be effected before or after infection by the harmful fungi.

USE EXAMPLE

Activity Against *Botrytis cinerea*

The active ingredients, separately or together, were formulated as a 10% emulsion in a mixture of 70% by weight of cyclohexanone, 20% by weight of Nekanil® LN (Lutensol® AP6, wetting agent having emulsifying and dispersing action based on ethoxylated alkylphenols) and 10% by weight of Emulphor® EL (Emulan® EL, emulsifier based on ethoxylated fatty alcohols) and diluted with water to give the desired concentration.

After bell pepper seedlings cv. "Neusiedler Ideal Elite" had properly developed 4–5 leaves, they were sprayed to run-off with aqueous suspensions comprising 80% by weight of active ingredient and 20% by weight of emulsifier in the dry matter. After the spray coating had dried on, the plants were sprayed with a conidia suspension of the fungus *Botrytis cinerea* and placed in a chamber at high atmospheric humidity and 22–24° C. After 5 days, the disease on the untreated control plants had developed to such an extent that the resulting foliar necroses covered most of the leaves.

Evaluation was carried out by determining the infected leaf areas in percent. These percentages were converted into efficacies. The efficacy (W) was determined as follows using Abbot's formula:

$$W = (1-\alpha) \cdot 100/\beta$$

$\alpha$ is the degree of fungal infection of the treated plants in % and $\beta$ is the degree of fungal infection of the untreated (control) plants in %

At an efficacy of 0, the infection level of the treated plants corresponds to that of the untreated control plants; at an efficacy of 100, the treated plants were not infected.

The expected efficacies of the mixtures of the active ingredients were determined using Colby's formula [R. S. Colby, Weeds 15, 20–22 (1967)] and compared with the observed efficacies.

Colby's formula: $E = x + y - x \cdot y/100$

E expected efficacy, expressed in % of the untreated control, when using the mixture of the active ingredients A and B at concentrations of a and b x efficacy, expressed in % of the untreated control, when using active ingredient A at a concentration of a y efficacy, expressed in % of the untreated control, when using active ingredient B at a concentration of b The synergistc action of the mixtures according to the invention was demonstrated by the following experiments:

USE EXAMPLES

The experiments were carried out using the following compounds:

I.A corresponds to Compound I.32 of the table on page 3 of the application

I.B corresponds to Compound I.38 of the table on page 3 of the application

II corresponds to formula II

Use Example 1

Activity Against *Phytophthora infestans*

Leaves of plants of the cultivar "GroBe Fleischtomate" in pots were sprayed to run-off with an aqueous suspension made with a stock solution of 10% of active ingredient, 63% of cyclohexanone and 27% of emulsifier. The next day, the leaves were infected with an aqueous zoospore suspension of *Phytophthora infestans*. The plants were subsequently placed in a water-vapor-saturated chamber at from 16 to 18° C. After 6 days, the tomato blight had developed on the untreated, but infected, control plants to such an extent that it was possible to evaluate the disease level visually in %.

The visually determined values for the percentage of infected leaf area were converted into efficacies as % of the untreated control. An efficacy of 0 is the same disease level as in the case of the untreated control, an efficacy of 100 is a disease level of 0%. The expected efficacies for combinations of active ingredients were determined using Colby's formula (Colby, S. R. (Calculating synergistic and antagonistic responses of herbicide Combinations", Weeds, 15, pp. 20–22, 1967) and compared with the observed efficacies.

Untreated control: disease level 88%

TABLE 1.1

Efficacies of the individual active ingredients

| Active ingredient | Concentration of active ingredient in the spray mixture in ppm | Efficacy in % of the untreated control |
|---|---|---|
| I.A | 3.1 | 55 |
|  | 0.2 | 21 |
| I.B | 0.2 | 21 |
| II | 3.1 | 66 |
|  | 0.2 | 9 |

TABLE 1.2

Efficacies of the mixture

| Active ingredient mixture | Observed efficacy | Expected efficacy* |
|---|---|---|
| 3.1 ppm I.A + 3.1 ppm II Mixing ratio 1:1 | 100 | 85 |
| 0.2 ppm I.A + 0.2 ppm II Mixing ratio 1:1 | 66 | 28 |
| 0.2 ppm I.B + 0.2 ppm II Mixing ratio 1:1 | 43 | 28 |

*)calculated using Colby's formula

The experimental results reveal that the observed efficacy in all mixing ratios is higher than the efficacy calculated before-hand using Colby's formula.

Use Example 2

Efficacy Against *Botrytis cinerea* on Bell Pepper Fruits

Disks of green bell pepper fruits were sprayed to run-off with an aqueous preparation of active ingredient made with a stock solution of 10% of active ingredient, 63% of cyclohexanone and 27% of emulsifier. 2 hours after the spray coating had dried on, the fruit disks were inoculated with a spore suspension of *Botrytis cinerea*, containing $1.7 \times 10^6$ spores per ml in a 2% strength Biomalz solution. The inoculated fruit disks were subsequently incubated for 4 days in humid chambers at 18° C. The level of Botrytis infection on the diseased fruit disks was then evaluated visually.

The visually determined values for the percentage of infected leaf area were converted into efficacies as % of the untreated control. An efficacy of 0 is the same disease level as in the case of the untreated control, an efficacy of 100 is a disease level of 0%. The expected efficacies for combinations of active ingredients were determined using Colby's formula as mentioned above and compared with the observed efficacies.

Untreated control: disease level 97%

TABLE 2.1

Efficacies of the individual active ingredients

| Active ingredient | Concentration of active ingredient in the spray mixture in ppm | Efficacy in % of the untreated control |
| --- | --- | --- |
| I.A | 12.5 | 59 |
|  | 0.8 | 2 |
| II | 12.5 | 0 |
|  | 0.8 | 0 |

TABLE 2.2

Efficacies of the mixture

| Active ingredient mixture | Observed efficacy | Expected efficacy*) |
| --- | --- | --- |
| 12.5 ppm I.A + 12.5 ppm II Mixing ratio 1:1 | 89 | 59 |
| 0.8 ppm I.A + 0.8 ppm II Mixing ratio 1:1 | 28 | 2 |

*)calculated using Colby's formula

The experimental results reveal that the observed efficacy in all mixing ratios is higher than the efficacy calculated before-hand using Colby's formula.

Use Example 3

Efficacy Against *Botrytis cinerea* on Bell Peppers

Bell pepper seedlings cv. "Neusiedler Ideal Elite" which had 4–5 well-developed leaves were sprayed to run-off with an aqueous preparation of active ingredient made with a stock solution of 10% active ingredient, 63% of cyclohexanone and 27% of emulsifier. The next day, the treated plants were inoculated with a spore suspension of *Botrytis cinerea* containing $1.7 \times 10^6$ spores/ml in a 2% strength aqueous Biomalz solution. The test plants were then placed into a controlled-environment cabinet at 22 to 24° C. and high atmospheric humidity. After 5 days, the extent of fungal disease on the leaves weas determined visually in %.

The visually determined values for the percentage of infected leaf area were converted into efficacies as % of the untreated control. An efficacy of 0 is the same disease level as in the case of the untreated control, an efficacy of 100 is a disease level of 0%. The expected efficacies for combinations of active ingredients were determined using Colby's formula as mentioned above and compared with the observed efficacies.

Untreated control: disease level 72%

TABLE 3.1

Efficacies of the individual active ingredients

| Active ingredient | Concentration of active ingredient in the spray mixture in ppm | Efficacy in % of the untreated control |
| --- | --- | --- |
| I.B | 50 | 30 |
|  | 12.5 | 30 |
| II | 50 | 0 |
|  | 12.5 | 0 |

TABLE 3.2

Efficacies of the mixture

| Active ingredient mixture | Observed efficacy | Expected efficacy*) |
| --- | --- | --- |
| 50 ppm I.A + 50 ppm II Mixing ratio 1:1 | 89 | 30 |
| 12.5 ppm I.A + 12.5 ppm II Mixing ratio 1:1 | 58 | 30 |

*)calculated using Colby's formula

The experimental results reveal that the observed efficacy in all mixing ratios is higher than the efficacy calculated before-hand using Colby's formula.

We claim:

1. A fungicidal mixture comprising:

a) a carbamate of the formula I:

(I)

where X is CH, n is 0, 1 or 2 and R is halogen, $C_1$–C4-alkyl or C1–C4-haloalkyl, and when n is 2, the two R's can be the same or different radicals or a salt or adduct thereof, and b) tetrachloroisophthalonitrile II:

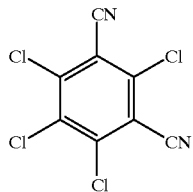

(II)

in a synergistically effective amount.

2. The composition of claim 1 wherein the ratio of compound (I) to compound (II) is 5:1 to 0.05:1.

3. The composition of claim 1 wherein the ratio of compound (I) to compound (II) is 1:1 to 0.05:1.

4. A composition of claim 1 which is conditioned in two parts, one part comprising compounds of the formula I as set forth in claim 1 in a solid or liquid carrier and the other part comprising the compound of formula II as set forth in claim 1 in a solid or liquid carrier.

5. A method of controlling harmful fungi, which comprises treating the harmful fungi, their environment, or the plants, seeds, soils, areas, materials or spaces to be kept free from them with a synergistically effective amount of a compound of the formula I or a salt or adduct thereof as set forth in claim 1 and the compound of the formula II as set forth in claim 1.

6. A method as claimed in claim 5, wherein a compound I or a salt or adduct thereof and the compound II are applied simultaneously together or separately, or in succession.

7. A method as claimed in claim 5 wherein a compound I or a salt or adduct thereof is applied at the rate of from 0.01 to 2.5 kg/ha.

8. A method as claimed in claim 5, wherein the compound II is applied at the rate of from 0.01 to 10 kg/ha.

* * * * *

UNITED STATES PATENT AND TRADEMARK OFFICE
CERTIFICATE OF CORRECTION

PATENT NO.: 6,136,840

DATED: October 24, 2000

INVENTOR(S): MUELLER et al.

It is certified that error appears in the above-identified patent and that said Letters Patent is hereby corrected as shown below:

On the cover page, insert the following:
--[30] Foreign Application Priority Data
  Aug. 30, 1996 [DE] Germany .................... 196 35 080.8--.

Col. 8, claim 1, line 65, "C$_1$-C4-alkyl" should be --C$_1$-C$_4$-alkyl--.

Col. 8, claim 1, line 66, "C1-C4-haloalkyl" should be --C$_1$-C$_4$-haloalkyl--.

Signed and Sealed this

Eighth Day of May, 2001

Attest:

NICHOLAS P. GODICI

Attesting Officer    Acting Director of the United States Patent and Trademark Office